US011439805B2

(12) United States Patent
Glaser

(10) Patent No.: US 11,439,805 B2
(45) Date of Patent: Sep. 13, 2022

(54) METHOD AND APPARATUS FOR ATTACHING A HOSE TO A DIMENSIONALLY STABLE SPOUT

(71) Applicant: FRESENIUS MEDICAL CARE DEUTSCHLAND GMBH, Bad Homburg (DE)

(72) Inventor: Benedict Glaser, Schweinfurt (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 0 days.

(21) Appl. No.: 16/475,263

(22) PCT Filed: Jan. 2, 2018

(86) PCT No.: PCT/EP2018/050043
§ 371 (c)(1),
(2) Date: Jul. 1, 2019

(87) PCT Pub. No.: WO2018/122404
PCT Pub. Date: Jul. 5, 2018

(65) Prior Publication Data
US 2019/0329018 A1 Oct. 31, 2019

(30) Foreign Application Priority Data
Jan. 2, 2017 (DE) .................. 10 2017 000 008.5

(51) Int. Cl.
A61M 39/12 (2006.01)
(52) U.S. Cl.
CPC ..... A61M 39/12 (2013.01); A61M 2205/0216 (2013.01); A61M 2205/3331 (2013.01); A61M 2207/00 (2013.01)

(58) Field of Classification Search
CPC .... A61M 39/12; A61M 2207/00; F16L 33/16; B23P 11/02; B23P 11/022
See application file for complete search history.

(56) References Cited

U.S. PATENT DOCUMENTS 1,322,843 A    11/1919  Townsend
2,498,357 A *   2/1950  Breisch ................ H01B 13/06
                                                       29/450
(Continued)

FOREIGN PATENT DOCUMENTS

CN    205397513    7/2016
DE    19520195     12/1996
(Continued)

OTHER PUBLICATIONS

Machine Translation of JP 2004-106151 (Year: 2004).*
(Continued)

Primary Examiner — Moshe Wilensky
Assistant Examiner — Kyle A Cook
(74) Attorney, Agent, or Firm — Jacobson Holman PLLC

(57) ABSTRACT

A method is provided for fitting an elastic hose onto a dimensionally stable connector, wherein the method involves the following steps: a) generating a flow of pressurized gas out of the connector; b) bringing the hose end to the connector against the flow direction of the gas out of the connector; and c) reducing the flow cross section of the hose beyond the connection point in order to generate dynamic pressure in the hose, widening the hose end; d) fitting the hose end onto the connector; and e) increasing the flow cross section of the hose beyond the connection point to mount the hose end to the outside of the connector.

11 Claims, 1 Drawing Sheet

(56) References Cited

U.S. PATENT DOCUMENTS

| | | | |
|---|---|---|---|
| 5,143,573 A | | 9/1992 | Ammon |
| 5,718,032 A | * | 2/1998 | Schneider |
| 2010/0012601 A1 | * | 1/2010 | Meshkinfam ........... A47L 19/04 |
| | | | 211/41.3 |
| 2013/0167607 A1 | * | 7/2013 | Adams ............... B21D 51/2669 |
| | | | 72/61 |
| 2015/0246475 A1 | * | 9/2015 | Suyama .................. B29C 49/58 |
| | | | 264/526 |
| 2016/0361481 A1 | * | 12/2016 | Lisitschew .............. F16L 33/00 |

FOREIGN PATENT DOCUMENTS

| | | |
|---|---|---|
| GB | 854724 | 11/1960 |
| JP | 2004-106151 | 4/2004 |

OTHER PUBLICATIONS

How do I mount a 9.8 mm tube onto a 10 mm metal pin? Mar. 13, 2016, https:/www.1-2-do.com/de/project/Wie-bringe-ich-einen-9 (translation included).

\* cited by examiner

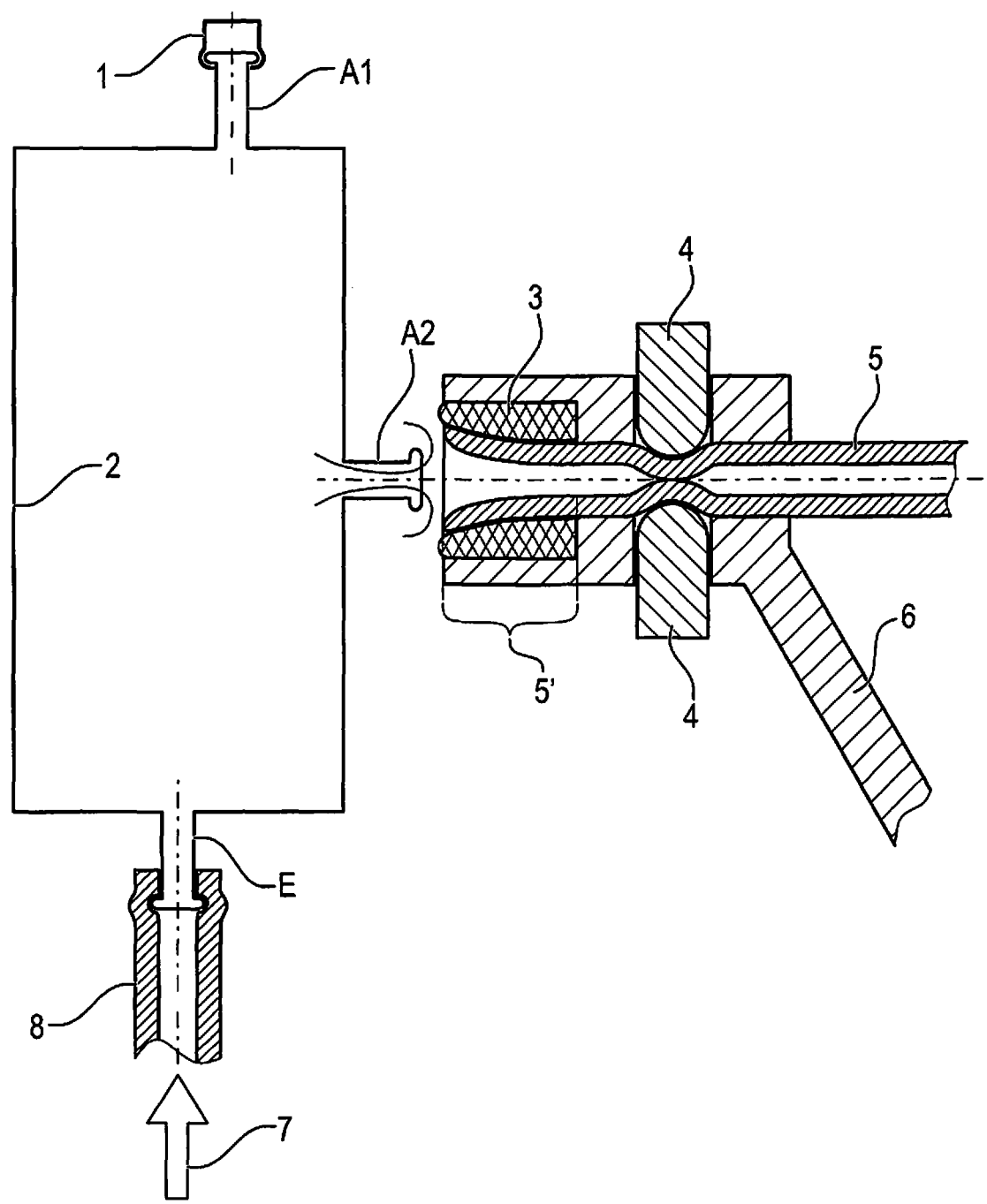

METHOD AND APPARATUS FOR ATTACHING A HOSE TO A DIMENSIONALLY STABLE SPOUT

The present invention relates to a method and to an apparatus for attaching an elastic hose to a dimensionally stable spout.

It is known from the prior art to attach hoses to components of dialysis machines or to spouts located at the components by hand to establish fluid connections. The components can, for example, be chambers, sensors, actuators, hydraulic connectors, etc.

It is a problem with this procedure that an elastic hose, i.e. a non-dimensionally stable object such as a silicone hose, has to be pushed onto a dimensionally stable spout without the hose being deformed in an inadmissible manner. The procedure is currently carried out by hand and the result of the attachment is visually monitored.

An automated attachment of the hoses is to be aimed for since the complex manual assembly procedure can be replaced with it. It is generally possible to have the procedures currently carried out by hand in an automated manner due to the advanced present state of automation technology and/or robotics. However, there is also the named problem in this respect that non-dimensionally stable hoses cannot easily be attached to a dimensionally stable spout without a deformation of the hose and thus a leak of a hydraulic system, etc., being able to occur.

A conceivable solution to this problem comprises a use of dimensionally stable end pieces or of connectors that are mounted at the hoses. This is, however, associated with an additional workstep and with cost disadvantages.

It is therefore the underlying object of the invention to further develop a method of the initially named type such that an attaching of a hose to a spout can be carried out reliably such that no deformation of the hose takes place.

The object is achieved by a method for attaching an elastic hose onto a dimensionally stable spout, wherein the method comprises the following steps: a) generating a flow of pressurized gas from the spout; b) guiding the hose end toward the spout against the direction of flow of the gas from the spout; and c) reducing the flow cross-section of the hose after the connection point for generating a dynamic pressure in the hose that expands the hose end; d) attaching the hose end to the spout; and e) increasing the flow cross-section of the hose after the connection point for applying the hose end to the outer side of the spout.

Provision is accordingly made that the method comprises the following steps that can be carried out in the order a) to e) or also in an order differing from this.

a) Generating a flow of pressurized gas from the spout;

b) guiding the hose end toward the spout against the direction of flow of the gas from the spout; and c) reducing the flow cross-section of the hose after the connection point for generating a dynamic pressure in the hose that expands the hose end;

d) attaching the hose end to the spout; and e) increasing the flow cross-section of the hose after the connection point for applying the hose end to the outer side of the spout; and/or reducing or ending the flow of the gas.

A dynamic pressure that expands the diameter of the hose end arises in the hose and that is to be attached to the spout due to the reduction of the flow cross-section of the hose after (i.e. downstream of the connection point between the hose end and the spout in the direction of flow of the gas flow). This diameter increase allows the hose end to be pushed over the spout, preferably without the hose end contacting the spout.

The connection point designates the longitudinal position at the hose that the end of the attached spout contacts.

Once the hose end has reached its desired position relative to the spout, the dynamic pressure in the hose is reduced or canceled such that the hose end is laid on the spout. This can take place, for example, in that the flow cross-section of the hose after the connection point is increased and/or in that the gas flow is reduced or fully discontinued.

It is pointed out that the term "hose end" does not comprise the actual front-side end of the hose, but rather a region having a specific length that also comprises the actual hose end.

The method in accordance with the invention can be carried out manually or also in an automated manner.

An attachment of a connector to the hose end is not necessary. An attachment of the hose to the spout without a deformation of the hose end arising is possible due to the widening of the free cross-section of the hose end.

The gas is preferably compressed air, but other gases can also be considered.

According to an optional modification of the invention, the gas, especially the compressed air, can be preheated. Preferably this means that the gas or compressed air is heated to a temperature above room temperature. The advantage of this is that the hose end expands more easily and/or more strongly.

Provision is made in a preferred embodiment of the invention that the spout is arranged at a component that has an inlet for the pressurized gas; and in that the method in accordance with step a) is carried out such that the gas flows in through the inlet of the component and flows out of the component through the spout in this case, the compressed air or the other gas flows into the component and out of the spout again through the inlet.

It is pointed out at this point that the terms "a" and "one" are not necessarily restricted to exactly one of the named elements, although this is a possible embodiment of the invention. A plurality of the elements in question are also covered by the terms. The component can, for example, have exactly one inlet or also a plurality of inlets.

A plurality of spouts are preferably arranged at the component, with the spouts to which no hose is to be attached in the upcoming workstep preferably being closed in an airtight manner. It is thus achieved that the compressed air, that is used in the following as representative for any desired gas, only or primarily exits that spout to which a hose is to be attached.

In a preferred embodiment, a closure cap cooperating in a shape-matching or force-transmitting manner with the spout is used for the airtight closing.

It is further preferred if the hose is held at and is attached to the spout by means of a hose assembly tool. Provision can be made in this respect that the reduction of the flow cross-section in accordance with step c) and/or the increase of the flow cross-section in accordance with step e) are carried out by means of the hose assembly tool. Other means can generally also be used for these steps.

It is particularly advantageous if the hose is widened in step c) such that it is pushed onto the spout without contacting the outer side of the spout. A deformation of the hose end is thus particularly reliably prevented.

The method can in particular be advantageously used when the spout is not conical at its outer side, but rather cylindrical. Conically tapering spouts are hygienically disadvantageous and are therefore not customary with dialysis machines. In the given connection, both circular cylinders and cylinders having different cross-sectional shapes (e.g. oval) are understood as cylindrical. Furthermore, not only those cylinders having a smooth surface are understood as cylinders, but also those having a wavy or grooved surface.

In order to be able to recognize that the hose is completely attached, provision can be made that the pressure is measured at a suitable point such as in the hose and/or in the spout and/or in the component and/or in the compressed air supply and an attached state of the hose is concluded on the reaching of a pressure limit value. The pressure increase is due to the fact that the ring gap between the hose end and the spout becomes smaller as the process of attachment progresses.

The method in accordance with the invention is preferably carried out at a blood treatment device and in particular at a dialysis machine.

The present invention furthermore relates to an apparatus for attaching an elastic hose to a dimensionally stable spout, wherein the apparatus comprises the following:

a) means for generating a flow of pressurized gas from the spout;

b) means for guiding the hose end toward the spout against the direction of flow of the gas from the spout;

c) means for reducing the flow cross-section of the hose after the connection point for generating a dynamic pressure in the hose that expands the hose end;

d) means for attaching the hose end to the spout; and e) means for increasing the flow cross-section of the hose after the connection point for applying the hose end to the outer side of the spout.

The apparatus can furthermore have holding means by means of which a component at which the spout is arranged is spatially fixed in a specific manner. The component such as a chamber, a sensor, an actuator, a hydraulic connector, etc., can thus be positioned in a defined manner in space, whereby the position of the spout(s) is fixed in space.

The means in accordance with features b) to e) can be formed by one and the same hose assembly tool or by different hose assembly tools.

In a possible embodiment of the invention, the hose assembly tool has at least two half-shells that engage around the hose, with provision preferably being made that the half-shells are formed from or comprise an elastic material, preferably an elastic plastic. The elastic material allows the widening of the hose cross-section for the purpose of attaching the hose to the spout.

The apparatus can furthermore have holding means for holding and moving closure caps that are suited and intended to close spouts that are not to be connected to a hose in an airtight manner.

The apparatus can furthermore be provided with a pressure sensor that is configured and arranged to measure the pressure in the spout and/or in the hose and/or in the compressed air supply and/or in the component or at another suitable point. The measured pressure value is reported to a processor that is configured to recognize the attached state of the hose end and/or to signal when the measured pressure value exceeds a limit value.

The device may also comprise a device for preheating the compressed air. The advantage of this is that the hose end expands more easily and/or more strongly.

According to a further embodiment of the device, the hose is configured such that it can be expanded more easily and/or more strongly with heated air. For example, this can be achieved upon using thermoplastics that are known to the skilled person.

The present invention finally relates to the use of an apparatus in accordance with the following description for attaching an elastic hose to a dimensionally stable spout of a blood treatment device, in particular of a dialysis machine.

The spout can, for example, consist of plastic or of metal.

Further details and advantages of the invention will be explained in more detail with reference to an embodiment shown in the drawing.

The only FIGURE shows a schematic sectional representation of the components participating in the attaching of a hose.

Reference numeral 2 denotes a component of a blood treatment device such as a chamber, a filter, etc.

The component has an inlet in the form of the spout E through which compressed air 7 flows through the hose 8 into the component 2. Reference numeral 7 denotes a controlled compressed air supply with pressure measurement. It is preferably purified compressed air.

The component 2 furthermore has two spout-like outlets A1 and A2 of which A1 is closed in a completely or largely airtight manner by a closure cap 1 and of which A2 is to be connected to the hose 5 in an airtight manner. The hose 5 can, for example, be a silicone hose.

Reference numeral 6 denotes the hose assembly tool that fixes the hose and that additionally has a slide valve 4 by means of which the hose can be cut off or whose flow can be restricted.

In its end region shown at the left in the FIGURE, the hose assembly tool 6 has an elastic and deformable hose mount 3 that receives the hose end 5' and allows a diameter increase of the hose end 5'. The hose end 5' can be longer than the spout A2 or can also have the same length.

As can be seen from the FIGURE, the spouts E, A1 and A2 are not conically tapering at their outer side, but rather cylindrical.

The process of attachment described in the following can take place manually or in an automated manner.

The component 2 is first placed into an assembly position, not shown, and is thus positioned at a defined location in space.

If the spouts E, A1 and A2 are not in fluid communication since the connection is cut off by valves, the latter are electrically contacted and thereby opened.

All the spouts (A1) except for two spouts (E, A2) are closed in an airtight or largely airtight manner. A closure cap 1 that closes around the spout A1 in a sealing manner is used for this purpose. The closure cap 1 consists of two half-shells that are latched to one another. The placing on of the closure cap 1 can take place in an automated manner, e.g. by picking by means of a robot and placing down and latching by an assembly tool.

The component 2 is then acted on by compressed air at a spout (E), as is marked by the arrow. The compressed air flows out of the open spout A2 and the pressure of the compressed air is measured, for example in the hose 8, in the component 2, etc.

A hose 5 is picked up at one end by the hose assembly tool 6 from a magazine at the assembly station. The hose assembly tool 6 closes off the hose 5 after the connection point to the spout A2 in an airtight manner by means of the cut-off 4.

The hose end 5' of the hose 5 is then guided toward the spout A2 by means of the hose assembly tool 6.

The hose assembly tool 6 has two half-shells that receive the hose 5 and that are produced from an elastic plastic. The hose 5 is thus held in position, on the one hand, and a widening of the hose end 5' is made possible, on the other hand.

The hose assembly tool 6 is guided further toward the spout A2. Due to the compressed air constantly flowing out of this spout and flowing into the hose end, an increasing dynamic pressure arises that becomes the larger, the closer the hose is guided toward the spout 5'. The ring gap between the hose end and the hose 5' becomes smaller.

The hose end 5' located in the region 3 thereby widens. A widening preferably takes place such that the inner diameter of the hose end 5' is larger than the outer diameter of the spout A2 such that the hose end 5' can be attached without contacting the spout A2.

The widened hose end 5' of the hose can now be guided over or attached to the spout A2.

Once this procedure is completed, the air pressure in the component 2 or in the hose 8 increases abruptly. This indicates the end of the attachment procedure. At the end of the attachment procedure, the hose assembly tool 6 releases the hose 5 and the cut-off element 4 is opened. The dynamic pressure thereby falls and the hose end 5' is laid all around the outer side of the spout A2.

If a hose is to be connected to a further spout A1, the latter's closure cap 1 is removed and the above-described procedure is repeated.

It is generally also conceivable to carry out the described connection procedure simultaneously at a plurality of spouts.

The spout E that serves the air supply is connected without compressed air to a hose at the end of the attachment process.

The described method is not restricted to one component. A plurality of components such as assemblies can generally be connected to one another in this manner since the compressed air is distributed over the hoses in the assembly.

The compressed air does not only serve the widening of the hose end, but rather also as a "sliding means" so that no residues of an e.g. gel lubricant have to be removed after the attachment.

The connection between the spout and the hose can be automatically monitored for leaks via the measured pressure.

The above-named steps can be carried out manually or in an automated manner.

The use of a robot having a robot arm is thus conceivable, for example, that can reach almost every position in space.

The use of a camera having image recognition is furthermore conceivable such that the robot can position the hose end exactly.

The invention claimed is:

1. A method for attaching an elastic hose onto a dimensionally stable spout, wherein the method comprises the following steps:
   a) generating a flow of pressurized gas from the spout;
   b) placing an end of the elastic hose in an elastic and deformable hose mount of a hose assembly tool;
   c) guiding the end of the hose toward the spout against a direction of the flow of the gas from the spout;
   d) reducing a flow cross-section of the hose after a connection point for generating a dynamic pressure in the hose that expands the hose end with the hose assembly tool by which the hose can be cut off or whose flow can be restricted, and wherein the elastic and deformable hose mount deforms to allow a diameter increase of the hose end;
   e) attaching the hose end to the spout; and
   f) increasing the flow cross-section of the hose after the connection point for applying the hose end to an outer side of the spout where the hose is held at and is attached to the spout by the hose assembly tool and such that the reduction of the flow cross-section in accordance with step d) and the increase of the flow cross-section in accordance with step f) are carried out by the hose assembly tool whereat the increase of the flow cross-section in accordance with step f) happens through releasing of the hose out of the hose assembly tool.

2. A method in accordance with claim 1, characterized in that the gas is compressed air and/or that the gas is heated.

3. A method in accordance with claim 1, characterized in that the method steps c) to f) are carried out manually or in an automated manner.

4. A method in accordance with claim 1, characterized in that the hose is widened in step d) such that it is pushed onto the spout without contacting the outer side of the spout.

5. A method in accordance with claim 1, characterized in that the spout is not conical, but rather cylindrical at its outer side.

6. A method in accordance with claim 1, characterized in that a pressure in the hose and/or in the spout and/or in the component and/or in the compressed air supply is measured; and in that an attached state of the hose is concluded when a limit pressure value is reached.

7. A method in accordance with claim 1, characterized in that the spout is located at a blood treatment device.

8. A method in accordance with claim 1, characterized in that the spout is located at a dialysis machine.

9. A method in accordance with claim 1, characterized in that the spout is arranged at a component that has an inlet for the pressurized gas; and in that the method in accordance with step a) is carried out such that the gas flows in through the inlet of the component and flows out of the component through the spout.

10. A method in accordance with claim 9, characterized in that the dimensionally stable spout is one of a plurality of spouts arranged at the component; and in that the spouts onto which no hose is to be attached are closed in an airtight manner.

11. A method in accordance with claim 9, characterized in that the dimensionally stable spout is one of a plurality of spouts arranged at the component; and in that the spouts onto which no hose is to be attached are closed in an airtight manner, with a closure cap being used for the airtight closing that cooperates with the spout in a shape-matching and/or force-transmitting manner.

* * * * *